(12) United States Patent
Malin (10) Patent No.: US 9,995,525 B2
(45) Date of Patent: Jun. 12, 2018

(54) LOW-TEMPERATURE AUTOMATED STORAGE FOR LABORATORY SAMPLES WITH AUTOMATED ACCESS

(75) Inventor: Cosmas G. Malin, Mauren (LI)

(73) Assignee: LICONIC AG, Mauren (LI)

( * ) Notice: Subject to any disclaimer, the term of this patent is extended or adjusted under 35 U.S.C. 154(b) by 1858 days.

(21) Appl. No.: 12/689,701

(22) Filed: Jan. 19, 2010

(65) Prior Publication Data

US 2010/0183408 A1  Jul. 22, 2010

(30) Foreign Application Priority Data

Jan. 19, 2009  (CH) ...................................... 0078/09

(51) Int. Cl.
| | |
|---|---|
| F25D 16/00 | (2006.01) |
| F25D 25/04 | (2006.01) |
| F25D 3/11 | (2006.01) |
| G01N 1/42 | (2006.01) |
| B01L 7/00 | (2006.01) |
| G01N 35/00 | (2006.01) |

(Continued)

(52) U.S. Cl.
CPC ................ *F25D 16/00* (2013.01); *B01L 7/50* (2013.01); *F25D 3/11* (2013.01); *F25D 25/04* (2013.01); *G01N 1/42* (2013.01); *G01N 35/0099* (2013.01); *B01L 9/52* (2013.01); *G01N 2035/0425* (2013.01)

(58) Field of Classification Search
CPC ........ B01L 3/5085; B01L 7/525; F25D 11/02; F25D 13/02; F25D 13/04; F25D 23/02; F25D 23/123; F25D 25/00; F25D 25/005; F25D 25/02; F25D 25/04; F25D 23/021; G01N 2035/0425

USPC ........... 62/266, 378, 382, 374, 265; 414/281
See application file for complete search history.

(56) References Cited

U.S. PATENT DOCUMENTS

| | | | | |
|---|---|---|---|---|
| 2,165,513 A | * | 7/1939 | Smith | ............................. 62/302 |
| 4,250,266 A | | 2/1981 | Wade | |
| 4,696,902 A | | 9/1987 | Bisconte | |

(Continued)

FOREIGN PATENT DOCUMENTS

| | | |
|---|---|---|
| CH | 696 326 | 4/2007 |
| DE | 689 11 315 | 3/1994 |

(Continued)

OTHER PUBLICATIONS

European Search Report/Office Action conducted in counterpart European Appln. No. 10 405 009.1-1602 (dated Oct. 29, 2015).

(Continued)

*Primary Examiner* — Anna M Momper
*Assistant Examiner* — Brendan P Tighe
(74) *Attorney, Agent, or Firm* — Greenblum & Bernstein, P.L.C.

(57) ABSTRACT

The storage comprises, from the bottom to the top, a low temperature storage zone, for storing the samples, a handling zone, housing at least part of an automatic transport device, and an access zone, where the user can enter for maintenance. A separating wall consisting of removable panels insulates the access zone, for the rooms below it. A peripheral housing, contains a peripheral chamber for temporarily storing the samples at slightly higher temperatures. A liquid nitrogen container, is used to feed dry gas to the storage zone and to maintain it under slight overpressure for preventing the entry of moisture.

9 Claims, 4 Drawing Sheets (51) Int. Cl.
  *B01L 9/00* (2006.01)
  *G01N 35/04* (2006.01)

(56) References Cited

U.S. PATENT DOCUMENTS

| | | | |
|---|---|---|---|
| 4,868,122 A | 9/1989 | Kominek et al. | |
| 4,907,889 A | 3/1990 | Simone | |
| 4,989,416 A | 2/1991 | Miller et al. | |
| 5,192,506 A | 3/1993 | Kureshy et al. | |
| 5,205,128 A | 4/1993 | Richard | |
| 5,233,844 A | 8/1993 | Knippscheer et al. | |
| 5,345,395 A | 9/1994 | Griner | |
| 5,435,685 A | 7/1995 | Tsuda et al. | |
| 5,470,744 A | 11/1995 | Astle | |
| 5,524,981 A * | 6/1996 | Herrmann et al. | 312/408 |
| 5,715,688 A | 2/1998 | Jones, III | |
| 5,735,587 A | 4/1998 | Malin | |
| 6,027,190 A | 2/2000 | Stewart et al. | |
| 6,129,428 A | 10/2000 | Helwig et al. | |
| 6,265,210 B1 | 7/2001 | Silley et al. | |
| 6,478,524 B1 | 11/2002 | Malin | |
| 6,568,770 B2 | 5/2003 | Gonska et al. | |
| 6,669,432 B2 | 12/2003 | Hamel et al. | |
| 6,673,595 B2 | 1/2004 | Barbera-Guillem | |
| 6,694,767 B2 * | 2/2004 | Junca et al. | 62/266 |
| 6,752,479 B2 | 6/2004 | Ferger et al. | |
| 6,881,572 B2 | 4/2005 | Fitzgerald et al. | |
| 7,013,197 B2 | 3/2006 | Melching et al. | |
| 7,021,730 B2 * | 4/2006 | Remmers | 312/404 |
| 7,100,396 B2 | 9/2006 | Melching et al. | |
| 7,314,341 B2 | 1/2008 | Malin | |
| 7,497,533 B2 * | 3/2009 | Remmers | 312/404 |
| 7,513,127 B2 * | 4/2009 | Owen et al. | 62/382 |
| 8,252,232 B2 * | 8/2012 | Neeper et al. | 422/65 |
| 2001/0043031 A1 | 11/2001 | Gonska et al. | |
| 2002/0063077 A1 | 5/2002 | Ferger et al. | |
| 2003/0020387 A1 * | 1/2003 | Wing et al. | 312/408 |
| 2004/0004415 A1 | 1/2004 | Melching | |
| 2004/0115101 A1 | 6/2004 | Malin | |
| 2005/0069401 A1 | 3/2005 | Malin | |
| 2005/0260102 A1 | 11/2005 | Angelantoni et al. | |
| 2006/0006774 A1 | 1/2006 | Jackson et al. | |
| 2006/0053825 A1 * | 3/2006 | Owen et al. | 62/441 |
| 2006/0063122 A1 | 3/2006 | Heeg et al. | |
| 2008/0231152 A1 | 9/2008 | Malin | |
| 2008/0272674 A1 | 11/2008 | Malin | |
| 2009/0026905 A1 | 1/2009 | Malin | |
| 2009/0098642 A1 | 4/2009 | Kiyota et al. | |
| 2012/0134897 A1 * | 5/2012 | Malin | 422/554 |

FOREIGN PATENT DOCUMENTS

| | | | |
|---|---|---|---|
| DE | 199 03 958 | 8/2000 | |
| EP | 0 035 452 | 9/1981 | |
| EP | 0 983 736 | 3/2000 | |
| EP | 1 172 724 | 1/2002 | |
| EP | 1 634 496 | 3/2006 | |
| EP | 1972874 | 9/2008 | |
| EP | EP2458308 A2 * | 5/2012 | F25D 13/02 |
| FR | 2 788 042 | 7/2000 | |
| GB | 2 228 989 | 9/1990 | |
| JP | 2004-131249 | 4/2004 | |

OTHER PUBLICATIONS

European Search Report conducted in counterpart European Appln. No. 10 40 5009.1-1602 (dated Jul. 10, 2015).

* cited by examiner

LOW-TEMPERATURE AUTOMATED STORAGE FOR LABORATORY SAMPLES WITH AUTOMATED ACCESS

CROSS REFERENCE TO RELATED APPLICATIONS

This application claims the priority of Swiss patent application 00078/09, filed Jan. 19, 2009, the disclosure of which is incorporated herein by reference in its entirety.

1. TECHNICAL FIELD

The invention relates to a low-temperature storage for laboratory samples with automated access.

In this context, the term "low-temperature" storage is to be understood as a storage adapted and structured to store samples at temperatures below −20° C., in particular below −50° C., in particular at approximately −80° C.

2. DISCUSSION OF BACKGROUND INFORMATION

Laboratory samples, such as organic and inorganic substances in suitable containers, sometimes have to be stored at very low temperatures, such as −80° C. Equipment for this purpose must provide a storage zone where a large number of different samples can be stored, sometimes for extended periods of time.

A storage of this type is described in EP 1 972 874.

Manual access to the storage zone should, in normal operation, be avoided because it would affect temperature stability. In addition, any humidity brought into the storage zone tends to freeze and to create ice deposits which, due to very low sublimation rates, tend to accumulate over time and to affect the operation of the device.

To alleviate this problem and in order to quickly access any of a large number of samples within the storage zone, the device according to EP 1 972 874 is equipped with an automated transport device.

A further problem faced by devices of this type is the fact that the low temperature can affect reliable operation of equipment, in particular of mechanically movable equipment adapted to manipulate the probes.

For this reason, the device of EP 1 972 874 comprises a handling zone located above the storage zone and being maintained at a higher temperature than the storage zone. The automated transport device is arranged at, least partially in the handling zone, where its components are not in thermal contact with the low-temperature storage zone.

SUMMARY OF THE INVENTION

Generally, the invention provides a low-temperature storage that is capable of storing samples at temperatures below −50° C. and that allows a manipulation of the probes with high reliability while being convenient to work with.

This problem is solved by an automated low-temperature storage for storing laboratory samples. The storage includes a storage zone for storing the samples that is maintained at a first temperature below −20° C., a handling zone located above the storage zone that is maintained at a second temperature above the first temperature and below 0° C., a chamber laterally adjacent to the storage zone and the handling zone for storing samples at a third temperature higher than the first temperature, wherein the third temperature is below 0° C. An opening connects the handling zone and the chamber, and an automated transport device is arranged at least partially in the handling zone and adapted and structured to move the samples between the storage zone, the handling zone and the chamber.

Accordingly, the storage is equipped with a storage zone for storing the samples at a first temperature below −50° C., such as approximately −80° C. A handling zone is located above the storage zone, and the device is structured and adapted to maintain a second temperature in the handling zone, with second temperature being below 0° C. but above the first temperature. The automated transport device is located at least partially in the handling zone.

In addition, the device is equipped with a chamber laterally adjacent to the storage and handling zones, i.e., separated from the same by a substantially vertical wall structure. An opening is provided for connecting the handling zone and the chamber. The transport device is structured and adapted to move samples between the storage zone, the handling zone and the chamber. The device is structured and adapted to maintain the chamber at a third temperature below 0° C. and above the first temperature.

The chamber arranged laterally adjacent to the storage and handling zones is easy to access by the user, e.g., for maintenance and/or for loading/removing samples. Its temperature does not have to be as low as the first temperature and can therefore be kept at levels where humidity problems are easier to control and the operation of equipment is not impaired.

Advantageously, no opening is provided for connecting the low-temperature storage zone and the chamber directly, such that the storage zone remains well insulated.

Another aspect of the invention relates to an automated low-temperature storage for storing laboratory samples. The storage includes a housing, a storage zone arranged in the housing for storing the samples that is maintained at a first temperature below −20° C., a handling zone arranged in said housing above said storage zone that is maintained at second temperature above the first temperature and below 0° C. An automated transport device is arranged at least partially in the handling zone and adapted and structured to access the samples in the storage zone, an access zone is arranged in the housing above the handling zone and is maintained at an access temperature above first temperature, and a separating wall separates the access zone and the handling zone. The separating wall is at least partially removable to provide access from the access zone to the handling zone and/or the to provide access from the access zone to the storage zone. Further, a manhole is located in the housing for providing user access to the access zone, and a door is provided for closing the manhole.

Hence, in a common housing, a storage zone, a handling zone and an access zone is provided. The storage zone is again maintained at a first temperature below −20° C., in particular below −50° C., and is provided for storing the samples. The handling zone is maintained at a second temperature above the first temperature and below 0° C., and the automated transport device is being arranged at least partially therein. The automated transport device is adapted and structured to access the samples in the storage zone, in order to e.g., exchange them with the chamber mentioned above and/or, in particular in the absence of such a chamber, with equipment located elsewhere.

The access zone, which is located above the handling zone, is also maintained at an access temperature above the first temperature. A separating wall is provided between the access zone and the handling zone. The separating wall is at least partially removable in the sense that an opening can be formed therein to provide access from the access zone to the handling zone and/or storage zone, e.g., to manually access the samples stored therein. A manhole is arranged in the housing for user access to the access zone. In this context, the term "manhole" is defined as any opening in the housing, be it in a horizontal or vertical wall thereof, which has suitable size to allow passage of a human user into the access zone. The manhole is closed by a door.

This design allows the user good access to the handling and/or storage zones, e.g. for maintenance work. The atmosphere in the access zone can be controlled to have a sufficiently low temperature and/or humidity in order to minimize the impact on the conditions within the handling and storage zones when the separating wall is opened.

A further aspect of the present invention is to provide a simple solution for mounting the storage racks that receive the samples in the storage zone.

In this aspect, the invention relates to an automated low-temperature storage for storing laboratory samples. The storage includes a storage zone arranged for storing the samples that is maintained at a first temperature below −20° C., an automated transport device adapted and structured to access the samples in the storage zone, at least one cooling unit for cooling the storage zone to the first temperature, and a gas supply adapted and structured to feed dry gas to the storage zone, and to maintain an overpressure in the storage zone.

Hence, a plurality of carriers extending from above into the storage zone is provided, with each carrier having a vertical mounting plate. Each mounting plate carries several storage racks, with the storage racks being hooked into the mounting plate.

By hooking the storage racks into the mounting plates, they can easily be mounted and removed by the user from above. At the same time, the mounting plate serves as a vertical guide for the storage racks while mounting them and holds the storage racks in an accurately defined position.

In yet a further aspect of the invention, a storage with a transport device is provided, in which problems due to ice are reduced.

In this aspect, the invention relates to an automated low-temperature storage for storing laboratory samples. The storage includes a storage zone arranged for storing the samples that is maintained at a first temperature below −20° C., an automated transport device adapted and structured to access the samples in the storage zone, at least one cooling unit for cooling the storage zone to the first temperature, and a gas supply adapted and structured to feed dry gas to the storage zone, and to maintain an overpressure in the storage zone.

Accordingly, the storage comprises a gas supply for dry gas, wherein "dry gas" designates any gas having a relative humidity below 20% at the temperature of the storage zone. The gas supply is adapted and structured to feed the dry gas to the storage zone and to maintain an overpressure therein. This measure prevents potentially humid gas from entering the storage zone, thereby minimizing the formation of ice deposits.

Advantageously, the gas supply is a liquid nitrogen container and the dry gas is nitrogen gas evaporated from the liquid nitrogen container. One advantage of this design lies in the fact that the continuous evaporation of the nitrogen gas provides sufficient overpressure for feeding the gas to the storage zone and for maintaining the overpressure therein.

Advantageously, the liquid nitrogen container can be used as a backup for cooling the storage in case that the cooling units of the storage should fail. For this purpose, a duct for carrying liquid nitrogen from the container to the storage zone is provided, as well as a valve for closing the duct.

Each of the four aspects of the invention can be either implemented individually, i.e., without the other aspects, or it can be combined with one or more of the other aspects.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE EMBODIMENTS OF THE INVENTION

Figure 1:
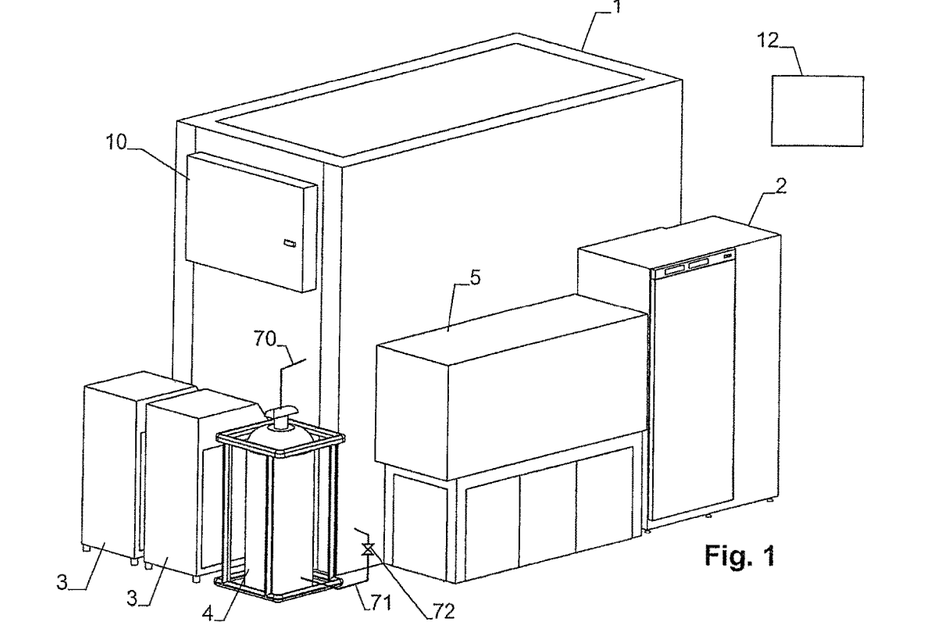
FIG. 1 is a view of a complete storage.

The storage of FIG. 1 includes a primary housing 1 that encloses the low-temperature section of the device. It further comprises a peripheral housing 2 enclosing a peripheral chamber, two redundant cooling units 3, a liquid nitrogen container 4 as well as further external sample handling hardware 5, all of which are advantageously arranged outside primary housing 1. In addition, the device is equipped with a control unit, schematically indicated under reference numeral 12, which controls the functions of its parts, and is responsible for maintaining climate and controlling the operations of the automatic transport device as described below. Control unit 12 can e.g., be located in a separate housing or within primary housing 1.

Figure 2:
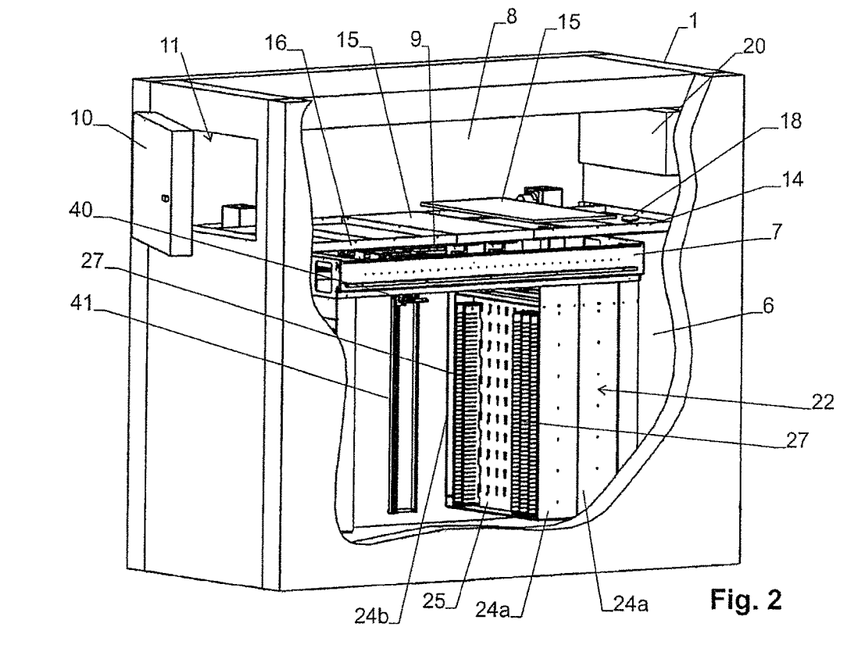
FIG. 2 is a view of the components within the primary housing of the storage.

FIG. 2 shows a set-up of the components within primary housing 1. The interior space of primary housing 1 is divided into three sections, which are, in the following, called the storage zone 6, the handling zone 7 and the access zone 8.

These components are described on more detail below.

Storage Zone:

Storage zone 6 forms the bottom most section of the interior of primary housing 1 and it is maintained at a low temperature, which is called the "first temperature" herein. The first temperature is a temperature below −50° C., in particular at approximately −80° C. Storage zone 6 generally receives and stores the samples for extended periods of time.

Handling Zone:

Handling zone 7 is located above storage zone 6 and is maintained at a second, higher temperature. The second temperature is, as mentioned, still typically below 0° C., in particular below −10° C., typically around −20° C. Handling zone 7 contains at least part of an automated transport device 9, whose purpose is to transport laboratory samples between storage zone 6 and the chamber described below. In particular, handling zone 7 advantageously holds the motors and other parts of transport device 9 that are poorly suited to operate at very low temperatures or that emit heat that might disturb the environment in storage zone 6.

Access Zone:

Access zone 8 forms the top section of the interior of primary housing 1 and is located above handling zone 7. Its purpose is to provide the user of the device with access to handling zone 7 and/or storage zone 6 for maintenance work.

Access zone 8 is advantageously sufficiently large for a user to enter, at least in kneeling or creeping fashion, and should in that case have a height of at least 50 cm.

Access zone 8 includes a door 10 closing a manhole 11. In the embodiment of FIG. 2, access zone 8 is elongate and door 10 is located at one vertical end wall of access zone 8.

The floor of access zone 8 is formed by a separating wall 14, which separates access zone 8 from handling zone 7. It comprises several gas-proof panels 15 located in a frame 16 that are structured to carry the weight of the user.

Each panel 15 can be lifted from frame 16 in order to form an access opening from access zone 8 into handling zone 7.

It must be noted that the panels 15 are only one of various possible embodiments of separating wall 14. For example, separating wall 14 may also comprise trapdoors or any other suitable structure that allows at least partial removal in order to provide access from access zone 8 to handling zone 7 and/or to storage zone 6.

The components within primary housing 1 further include an air dryer 20 arranged and structured to dry air in access zone 8. It can be used to remove humidity from access zone 8, such as humidity introduced when the user opens door 10 or exhales into the access zone 8.

Advantageously, at least one ventilator 18, or another device for enabling and disabling an atmosphere exchange through separating wall 14, such as a closeable flap or door, is arranged in separating wall 14 in order to optionally circulate air between access zone 8 and handling zone 7 and storage zone 6, thereby allowing to use dryer 20 for drying handling zone 7 and storage zone 6, e.g., before cooling storage zone 6 down to its operating temperature.

In normal operation of the device, access zone 8 is, as mentioned, maintained at an "access temperature", which is well above the temperature of storage zone 6. It may also be higher than the temperature in handling zone 7.

Sample Storage:

As shown in FIG. 2, several carriers 22 extend from above into storage zone 6. Each carrier 22 is suspended on a carriage located in handling zone 7. Each such carriage is displaceable therein along a longitudinal horizontal direction of the device.

Figure 5:
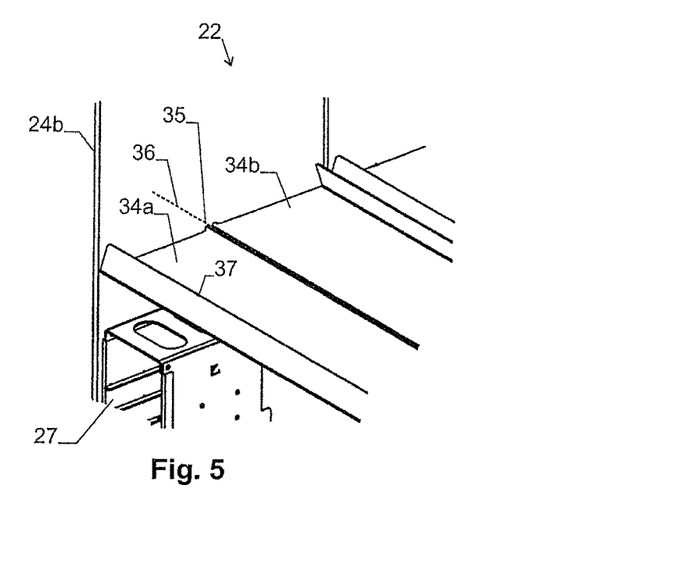
FIG. 5 shows the lids of a carrier.

Each carrier 22 comprises two spaced apart, parallel, vertical side walls 24a, 24b, see FIGS. 2 and 5. Further, each carrier 22 comprises a vertical mounting plate 25, extending between the side walls 24a, 24b and being arranged perpendicularly thereto.

Figure 3:
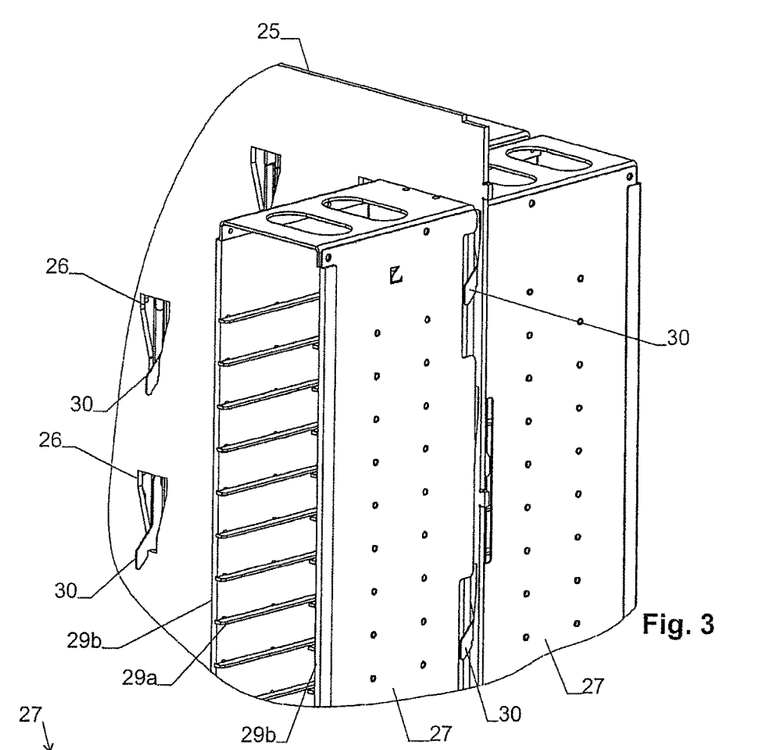
FIG. 3 shows two storage racks mounted to a mounting plate.

Mounting plate 25, which is illustrated in even greater detail in FIG. 3, is a flat sheet metal plate having a plurality of openings 26 formed therein.

To receive the samples, a plurality of storage racks 27 can be hooked to both sides of each mounting plate 25. As can best be seen in FIGS. 3 and 4, each storage rack 27 comprises a plurality of storage locations above each other, with each storage location being formed by two lateral ledges 29a mounted to lateral vertical side walls 29b of the storage rack 27.

Figure 4:
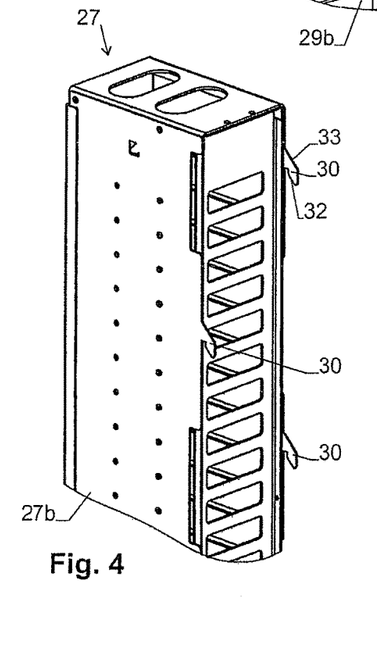
FIG. 4 shows a storage rack with its hooks.

For hooking the storage racks 27 onto the mounting plates 25, each storage rack 27 is provided with several hooks 30 at its, side facing mounting plate 25, see FIG. 3, 4. In the present embodiment, the hooks 30 are formed as projections of the side walls 27b of the racks, with each hook of the left side wall being located at a height in the middle of the two neighboring hooks of the right side wall and vice versa, such that the hooks of two storage racks 27 arranged directly opposite each other on mounting plate 25, as shown in FIG. 3, do not interfere with each other.

To mount a storage rack 30 to mounting plate 25, its hooks 30 are inserted into a suitable set of the openings 26 and engage the same.

As can be seen in FIG. 3, the openings 26 are tapered towards their bottom ends, such that they laterally guide and finally confine the hooks 30 engaged therein.

In addition, and as can be seen from FIG. 4, each hook comprises at least one guiding surface 32, in the present case formed by the inclined bottom edge thereof, which faces its respective storage rack 27 and is inclined to the vertical direction of the storage rack 27 (with the term "inclined" expressing the fact that the angle between the vertical direction and guiding surface 32 is clearly neither 0° nor 90° but somewhere in between). When a hook 30 is inserted into one of the openings 26 and then lowered, if guiding surface 32 abuts against the bottom edge of the opening, it pulls the hook into the opening and thereby the storage rack against the mounting plate.

Similarly, the top edge 33 of each hook 30, which faces away from its storage rack 27, is also inclined in respect to the vertical direction of storage rack 27 and serves to guide hook 30 into its respective opening 26 in case it abuts against the top edge of the opening.

As can further be seen from FIG. 5, each carrier 22 comprises a pair of lids 34a, 34b above the racks 27 carried by the carrier (only one of the racks 27 is shown in FIG. 5). The lids 34a, 34b serve to separate storage zone 6 at least partially from handling zone 7.

Each lid is a metal plate extending between the side walls 24a, 24b of its carrier and mounted thereto by hinges 35 defining a horizontal hinge axis 36 extending perpendicular to the side walls 24a, 24b. In a closed position, the lids 34a, 34b are arranged horizontally. To open a lid 34a, 34b, the user seizes a bent-up edge region 37 of the lid 34a, 34b and pivots it about hinge axis 36.

The purpose of the lids 34a, 34b is to insulate storage zone 6 at least partially from the hotter handling zone 7, and in particular from the heat of the motors of the transport device located in handling zone 7.

Transport Device:

The operation and design of transport device 9 substantially correspond to those of the transport device described in EP 1 972 874 and is not repeated in detail here.

In short, transport device 9 comprises a tray 40 mounted to a vertical guide 41, see FIG. 2. Guide 41 is suspended from a carriage running in rails in handling zone 7 and extends, while the carriage of the transport device 9 is being run along its rails, into a lateral gap formed between one set of side walls 24b of the carriers 22 and a neighboring vertical wall of primary housing 1. To access a storage position in the storage racks 27, the carriers 22 are horizontally displaced in such a manner that a gap forms between them at the location of storage position. Then, guide 41 is horizontally displaced into this gap while tray 40 is vertically displaced to the appropriate height in order to access the storage position.

Details of this mechanism are, as mentioned, described in EP 1 972 874.

Peripheral Chamber:

Advantageously, the present device is provided with a peripheral chamber laterally adjacent to storage zone 6 and handling zone 7 and separated from them by a vertical wall.

The peripheral chamber serves for temporarily storing the probes, e.g. when probes are to be introduced into the storage, removed from the storage, or handled by processing equipment or analytical equipment. As mentioned, the handling zone 8 is at a third temperature higher than the first (lowest) temperature, e.g. at −20° C. The third temperature will generally be similar or equal to the second temperature, i.e., to the temperature in handling zone 7.

Figure 6:
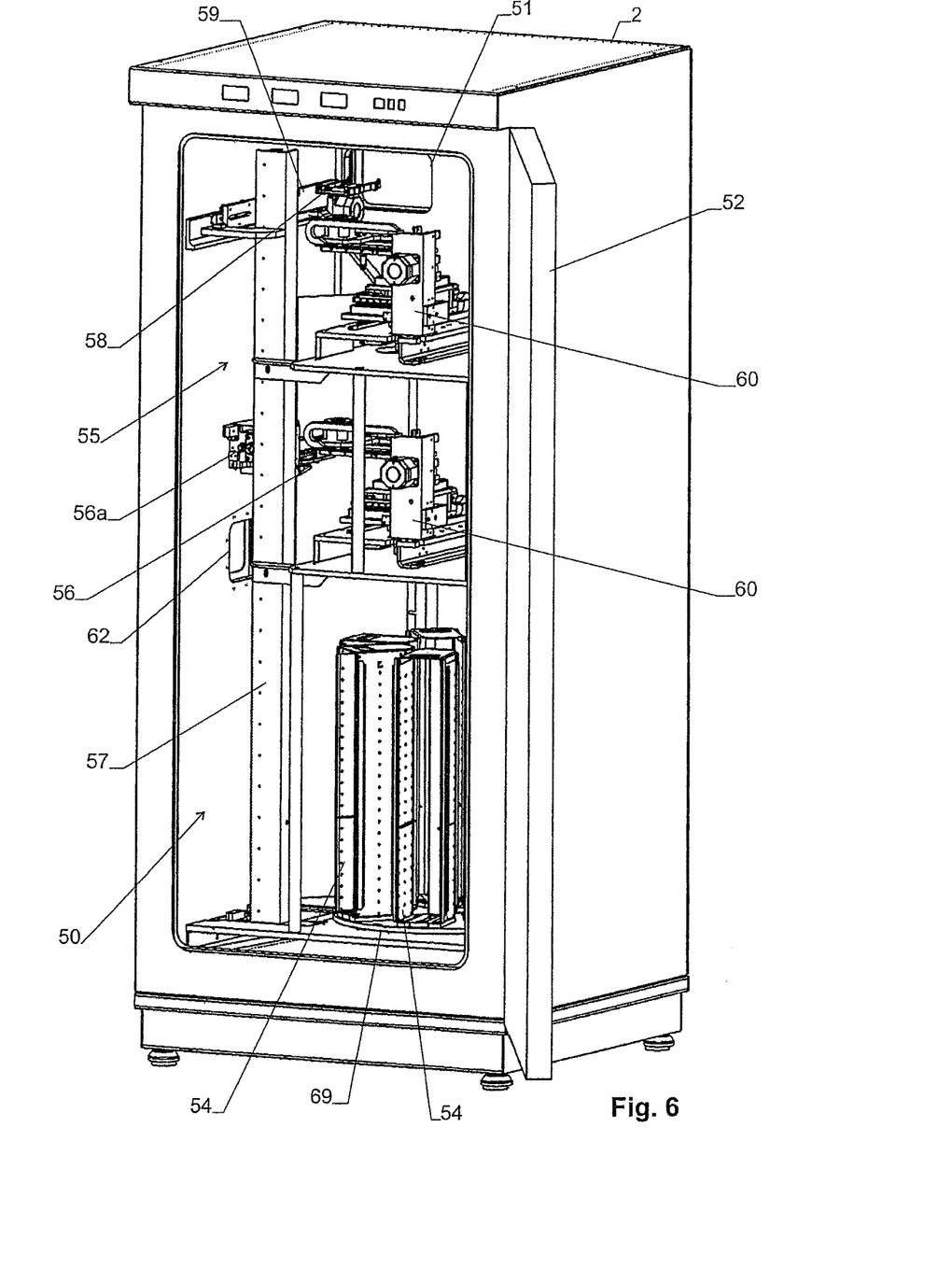
FIG. 6 shows the peripheral chamber in its housing.

In the embodiment shown in FIG. 1, and depicted in detail in FIG. 6, peripheral chamber 50 is located in peripheral housing 2, i.e., outside primary housing 1. Peripheral housing 2 is mounted with its back side against primary housing 1, and an opening 51 is provided that connects peripheral chamber 50 to handling zone 7. Transport device 9, which can include a first part located in handling zone 7 and a second part located in peripheral chamber 50, is adapted to move the samples from storage zone 6 through handling zone 7 into peripheral chamber 50 and back.

Peripheral housing 2 includes a user-operatable door 52, which, when opened, provides user access to peripheral chamber 50. Door 52 is located at the front side of peripheral housing 2, i.e., in the wall of peripheral housing 2 that is opposite to opening 51.

Advantageously, at least one storage rack 54 for temporarily storing a plurality of samples above each other is located in peripheral chamber 50. In the embodiment of FIG. 6, a plurality of such storage racks 54 are located on a rotatable carousel table 69.

The transport device 9 includes a manipulator 55 for automatically manipulating the samples in peripheral chamber 50. Manipulator 55 comprises a loading tray 56 on a lift carriage 56a, which can be displaced along a vertical guide bar 57. Tray 56 can further be rotated about a vertical axis. Manipulator 55 further comprises a transfer station 58. Transfer station 58 is mounted to a telescopic arm 59, which can be operated to extend through opening 51 into handling zone 7, where a sample can be loaded/unloaded to/from transfer station 58. On the other hand, arm 59 can be retracted, in which position loading tray 56 can pick up and deposit probes from/onto transfer station 58.

Once it is on loading tray 56, the sample can be displaced vertically, either to bring it to the location of various laboratory equipment, such as the stations 60 for handling individual tubes of the probes as shown in FIG. 6, or it can be brought to the location of the storage racks 54, where the sample can be stored.

As can be seen in FIG. 6, peripheral housing 2 may comprise a further opening 62, e.g., in a lateral side wall thereof, which allows to transfer probes to external sample hardware 5 (see FIG. 1), again by loading tray 56.

Figure 7:
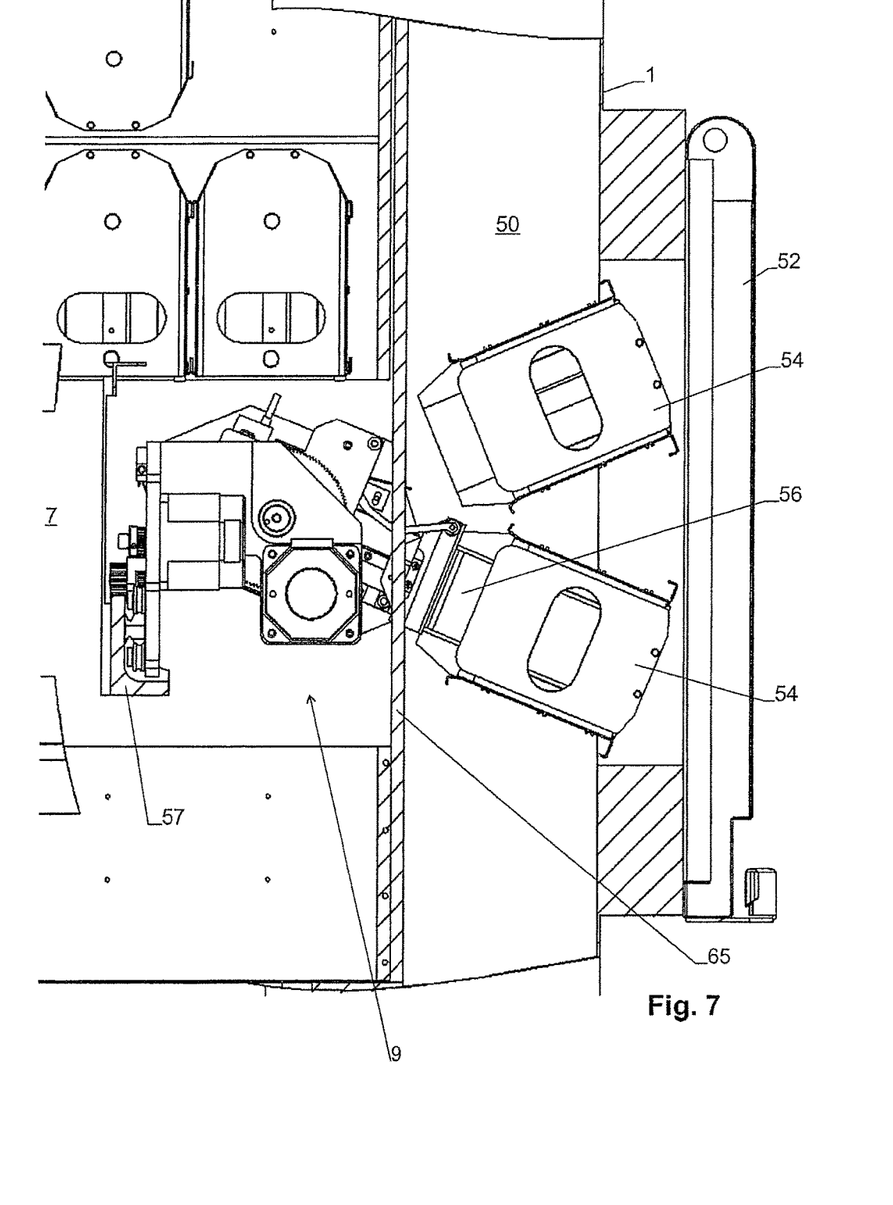
FIG. 7 is a top sectional view of an alternative embodiment of the peripheral chamber.

An alternative embodiment is shown in FIG. 7, where peripheral chamber 50 is formed within primary housing 1. In this embodiment, two storage racks 54 are located within storage location 50, each of which can receive several samples and can be accessed by transport device 9.

Transport device 9 comprises a vertical guide bar 57 and a tray 56 vertically displaceable along guide bar 57 as well as horizontally pivotal about a vertical axis in order to access the two storage racks 54. Guide bar 57 and tray 56 may be the same parts as guide 41 and tray 40 of FIG. 2, or they may be formed by separate components.

A vertical wall 65 separates peripheral chamber 50 from handling zone 7 and storage zone 6. An opening (not shown) is arranged in wall 65 for providing tray 56 with access to the storage racks 54. A door 52 is located opposite to this opening and is e.g. used for replacing the storage racks 54.

Climate Control:

The low temperature within the storage is primarily maintained by the cooling units 3 under control of control unit 12. In addition, liquid nitrogen container 4 is connected through a first duct 70 and a second duct 71 to the interior primary housing 1, advantageously directly to storage zone 6.

First duct 70 is connected to container 4 in such a way that it collects the evaporated nitrogen, which is produced by the continuously simmering nitrogen in container 4, and transports it to storage zone 6. Advantageously, duct 70 remains always open.

Second duct 71 is connected to container 4 in such a way that it conveys liquid nitrogen into handling zone 6 or any sections of the device thermally connected to handling zone 6. Second duct 71 can be closed by a valve 72. Valve 72 can be controlled manually and/or by control unit 12.

In normal operation, valve 72 is closed. The natural evaporation rate of the nitrogen in nitrogen container 4 provides a sufficient amount of gaseous nitrogen continuously flowing through duct 70 into storage zone 6 in order to maintain an overpressure therein. Since the evaporated nitrogen is dry, this prevents humidity from entering storage zone 6 is forming ice deposits therein.

Instead of a nitrogen container 4, another gas source providing sufficiently dry gas can be used to maintain a dry atmosphere under slight overpressure within storage zone 6.

A further important function of nitrogen container 4 is to provide reliable cooling for storage zone 6 even if the cooling units 3 fail. Since the liquid nitrogen is very cold, while it lasts it prevents the temperature in storage zone 6 to rise even if the cooling units 3 are unable to cool it. Hence, in case of a failure of the cooling units 3, e.g., due to a power loss, valve 72 can be opened manually or automatically and liquid nitrogen can be guided through duct 71 for cooling storage zone 6.

In other words, control unit 12 is adapted and structured to control the flow of the evaporated nitrogen from nitrogen container 4 to storage zone 6 such that
  in normal operation, the overpressure in storage zone 6 is maintained by the evaporated nitrogen from liquid nitrogen container 4, while the first in storage zone 6 is maintained by the cooling unit(s) 3, and
  upon a failure of the cooling unit(s) 3, the overpressure and the temperature in storage zone 6 are maintained by the evaporated nitrogen.

This control procedure is programmed into control unit 12 as a method for controlling the storage. Such a method is also part of the present invention.

The term "sample" as used herein encompasses the substance to be stored and, optionally, a container for one or more such substances. For example, the sample can be a bottle containing a single substance, or it can be a microtiter plate or a tube carrier carrying a plurality of substances.

While there are shown and described presently preferred embodiments of the invention, it is to be distinctly understood that the invention is not limited thereto but may be otherwise variously embodied and practiced within the scope of the following claims.

The invention claimed is:

1. An automated low-temperature storage for storing laboratory samples, the storage comprising:
  a storage zone arranged for storing the samples that is maintainable at a first temperature below −20° C.;
  a handling zone arranged above the storage zone that is maintainable at second temperature above the first temperature;

an automated transport device being arranged at least partially in the handling zone and being structured and arranged to access the samples in the storage zone;

a plurality of carriers extending from above into the storage zone, wherein each carrier comprises a vertical mounting plate; and a plurality of storage racks for receiving the samples, wherein each storage rack comprises a plurality of storage locations above each other, and wherein each mounting plate carries several storage racks, which are structured to be hooked into the mounting plate.

2. The storage of claim 1, further comprising a control device structured and arranged to maintain the first temperature and the second temperature.

3. The storage of claim 1, wherein each mounting plate comprises a plurality of openings and each storing rack has hooks to engage several of the plurality of openings.

4. The storage of claim 3, wherein the openings are tapered towards a bottom of the mounting plate in order to laterally guide and confine the hooks.

5. The storage of claim 3, wherein the hooks comprise at least one guiding surface facing a respective storage rack, and the guiding surfaces are inclined to a vertical direction of the storage racks in order to pull the storage racks towards the mounting plates when the storage racks are hooked into the mounting plates.

6. The storage of claim 1, further comprising lids mounted to the carriers above the racks for separating the storage zone from the handling zone.

7. The storage of claim 1, wherein each carrier comprises two vertical side walls with the mounting plate extending between the side walls.

8. The storage of claim 7, further comprising lids mounted to the carriers above the racks for separating the storage zone from the handling zone,
wherein the lids are mounted to the side walls and extend between the side walls.

9. The storage of claim 8, wherein the lids are pivotal about an axis perpendicular to the side walls.

* * * * *